(12) United States Patent
Castro Feo et al.

(10) Patent No.: US 11,241,516 B2
(45) Date of Patent: Feb. 8, 2022

(54) BIOMATERIAL SCAFFOLD FOR REGENERATING THE ORAL MUCOSA

(71) Applicant: HISTOCELL, S.L., Derio (ES)

(72) Inventors: María Begoña Castro Feo, Leioa (ES); Amparo Baiget Orts, Valencia (ES)

(73) Assignee: HISTOCELL, S.L., Derio (ES)

( * ) Notice: Subject to any disclaimer, the term of this patent is extended or adjusted under 35 U.S.C. 154(b) by 109 days.

(21) Appl. No.: 15/520,986

(22) PCT Filed: Oct. 23, 2015

(86) PCT No.: PCT/EP2015/074610
§ 371 (c)(1),
(2) Date: Apr. 21, 2017

(87) PCT Pub. No.: WO2016/062862
PCT Pub. Date: Apr. 28, 2016

(65) Prior Publication Data
US 2017/0340771 A1    Nov. 30, 2017

(30) Foreign Application Priority Data

Oct. 24, 2014  (EP) ..................................... 14382417

(51) Int. Cl.
| | |
|---|---|
| A61L 27/52 | (2006.01) |
| A61L 27/22 | (2006.01) |
| A61L 27/26 | (2006.01) |
| A61L 27/56 | (2006.01) |
| A61L 27/20 | (2006.01) |
| A61L 27/38 | (2006.01) |

(52) U.S. Cl.
CPC .............. *A61L 27/225* (2013.01); *A61L 27/20* (2013.01); *A61L 27/26* (2013.01); *A61L 27/38* (2013.01); *A61L 27/52* (2013.01); *A61L 27/56* (2013.01); *A61L 2430/34* (2013.01)

(58) Field of Classification Search
CPC ........ A61L 27/225; A61L 27/20; A61L 27/26; A61L 27/52
See application file for complete search history.

(56) References Cited

U.S. PATENT DOCUMENTS

| | | | |
|---|---|---|---|
| 4,438,198 A | 3/1984 | Schmer | |
| 6,506,727 B1 | 1/2003 | Hansson et al. | |
| 6,890,531 B1 | 5/2005 | Horie et al. | |
| 2008/0220524 A1 | 9/2008 | Noll et al. | |
| 2012/0269776 A1 | 10/2012 | Alaminos Mingorance et al. | |
| 2013/0079421 A1* | 3/2013 | Aviv | A61L 27/20 514/773 |

FOREIGN PATENT DOCUMENTS

| | | |
|---|---|---|
| CN | 103908693 A | 7/2014 |
| EP | 2594295 A1 | 5/2013 |
| KR | 2011/0023399 A | 3/2011 |
| WO | WO-03007873 A2 | 1/2003 |
| WO | WO 2011/023843 A2 | 3/2011 |
| WO | WO 2013/072409 A1 | 5/2013 |

OTHER PUBLICATIONS

Zhang et al. "Physically crosslinked hydrogels from polysaccharides prepared by freeze-thaw technique" (2013), Reactive & Functional Polymers, vol. 73: 923-928. (Year: 2013).*
O'Brien et al. Influence of freezing rate on pore structure in freeze-dried collagen-GAG scaffolds, 2004, Biomaterials 25: 1077-1086 (Year: 2004).*
Alaminos et al. Construction of a Complete Rabbit Cornea Substitute Using a Fibrin-Agarose Scaffold, 2006, Investigative Opthamology & Visual Science 47(8): 3311-3317) (Year: 2006).*
Ionescu et al. "Investigating a novel nanostructured fibrin-agarose biomaterial for human cornea tissue engineering: Rheological properties" Journal of Mechanical Behavior and Biomedical Materials 4(8): 1963-1973 (Year: 2011).*
"Appendix B: Agarose Physical Chemistry," Molecular Biology Research Products Catalog and Sourcebook for Electrophoresis 2009-2010, pp. 207-209 (2010).
International Search Report and Written Opinion of the International Searching Authority corresponding to European patent application serial No. PCT/EP2015/074610 dated Aug. 1, 2016.
IPRP of the International Searching Authority corresponding to European Patent Application Serial No. PCT/EP2015/074610 dated Apr. 25, 2017.

* cited by examiner

*Primary Examiner* — Taeyoon Kim
*Assistant Examiner* — Alexandra F Connors
(74) *Attorney, Agent, or Firm* — Jenkins, Wilson, Taylor & Hunt, P.A.

(57) ABSTRACT

The present invention refers to a process for preparing a biomaterial scaffold said method comprising, (a) providing a hydrogel comprising a fibrin network and a polysaccharide network; (b) subjecting the hydrogel of step a) to a freeze-thawing process to physically crosslink the hydrogel; and (c) subjecting the physically cross-linked hydrogel obtained after conducting the step b), to a lyophilization. The invention also relates to the biomaterial scaffold obtainable by the process as defined above, as well said biomaterial scaffold for its use to partially or completely increase, restore or replace the functional activity of a diseased or damaged oral mucosa.

15 Claims, 7 Drawing Sheets

BIOMATERIAL SCAFFOLD FOR REGENERATING THE ORAL MUCOSA

FIELD OF THE INVENTION

The present invention belongs to the field of tissue engineering, and more particularly to biomaterials suitable for regenerating, repairing, and/or replacing soft tissues.

BACKGROUND

A new, highly promising field of knowledge known as "Tissue Engineering" has been developed in medical and dental research over recent years. The main objectives of this innovative field are aimed at bioartificial regeneration, repair or replacement of the actual tissues and organs of the human body that were damaged by various factors, such as injuries, burn, by acquired diseases such as cancer or certain congenital abnormalities. Tissue engineering is based primarily on three fundamental components: 1) Cells, 2) Biomaterials, and 3) Biomolecules, inducers or growth factors.

In the case of biomaterials, they are used in the production of biological systems and applied in various branches of medicine. Among other characteristics, these materials are biocompatible due to their permanent contact with living tissues. Therefore, preventing unwanted reactions from occurring in the tissue-material interface and maintaining the biomaterial's properties throughout the time period in which it carries out its function are essential. Current studies focus on understanding the specific interactions between the physicochemical properties of the material, mechanical properties, and on the observation of cell behavior, such as cytokine and growth factor adhesion, activation and release. Today, there is a large amount of different biomaterials which can be classified as natural or synthetic polymeric, metallic or ceramic biomaterials according to their composition.

In Tissue Engineering, biomaterials must favor the biological and mechanical function of cells since they act as an artificial extracellular matrix. As a result, biomaterials can provide cells with a three-dimensional space to form new tissues with suitable structure and function.

Among soft tissues deficiencies, oral mucosa repair represents a challenging and necessary mission due to the complex structure of this tissue. The loss of oral mucosa as a result of various surgical procedures, injuries or other clinical conditions is a real problem in view of the need to obtain a suitable coverage that effectively repairs the created defect. The current solutions adopted with respect to this need involve the application of grafts from different donor sites and origins. However, these grafts present complications such as rejection (allografts, xenografts), donor site morbidity (autografts), maintenance of original tissue characteristics, provide enough structural properties to allow new tissue development while preventing collapse by surrounding tissues, limited functions and are aesthetically unappealing. These implications make it necessary to generate functional biological substitutes that are anatomically and aesthetically similar to the recipient site. Today, many research groups focus their research on the development of new biomaterials that provide a histological organization similar to the native tissue which, upon being transplanted, is effectively integrated in said native tissue, replacing the damaged tissue of the affected site with functional tissue. The creation of such biomaterials is currently deemed the best alternative for solving these problems involving rejection and the limited amount of tissue.

Biomaterials for oral mucosa regeneration must have mechanical and structural properties such as permeability, stability, elasticity, flexibility and plasticity and must adapt different desired forms, i.e., in sheets, as gels or solid three-dimensional structures. Ideally they also must induce new tissue formation by promoting surrounding cells and growth factors homing to injured site while the material degrades as new tissue remodeling progress.

WO 03/007873 discloses a freeze dried biocompatible porous matrix comprising fibrin which is crosslinked from fibrinogen in the presence of thrombin, Factor XIII and calcium chloride. The matrix may additionally include an auxiliary component, such as a polysaccharide, and can be used as an implant.

BRIEF DESCRIPTION OF THE INVENTION

The authors of the present invention have developed a new biomaterial characterized by having a macroporous scaffold structure which provides said material with a high strength, being easily handled in its swollen state and having stability, elasticity, flexibility and plasticity, as it can recover its shape after applying a deformation force. Furthermore, the biomaterial of the invention has shown to withstand a suture process in its swollen state without breaking or destroying, which assures correct fixing to the damaged tissue.

The biological tests have also pointed out the correct interaction of the biomaterial with cells, in particular human fibroblasts, keratinocytes, stem cells and other cell types related with soft tissues and oral mucosa repair, as well as a lack of cytotoxicity for said cells.

Additionally, the biomaterial of the invention has been tested in an in vivo model. The results confirm the absence of toxic events and favorable degradability rate overtime. Moreover, the biomaterial provides evident signs of neovascularization in early stages after implantation, and shows an adequate interaction with surrounding tissue, that it is capable to colonize the biomaterial of the present invention.

This biomaterial is synthesized by lyophilization of a hydrogel comprising a fibrin network and a polysaccharide network.

Thus, the first aspect of the present invention refers to a process (from now onwards process 1) for producing a biomaterial scaffold, said method comprising:
a) providing a hydrogel comprising a fibrin network and a polysaccharide network;
b) subjecting the hydrogel of step a) to a freeze-thawing process to physically crosslink the hydrogel; and
c) subjecting the physically cross-linked hydrogel obtained after conducting the step b), to a lyophilization.

A second aspect of the present invention refers to a biomaterial scaffold obtainable by the process 1 as defined above.

The hydrogel resulting from step b) of the process of the invention confers the biomaterial of the invention with improved mechanical properties as a result of the physical cross-linking derivable from the application of a freeze-thawing process. This freeze-thawing step provides a hydrogel having an interpenetrated network.

Therefore, another aspect of the present invention refers to a process (from now onwards process 2) for preparing a physically cross-linked hydrogel having an interpenetrating network, said process comprising:
a) providing a hydrogel comprising a fibrin network and a polysaccharide network; and b) subjecting the hydrogel of step a) to a freeze-thawing process.

A further aspect of the invention refers to a physically cross-linked hydrogel having an interpenetrating network obtainable by the process 2 as defined above.

Another aspect of the invention relates to a biomaterial scaffold as defined above for its use in medicine.

A fourth aspect of the invention relates to a biomaterial scaffold as defined above for its use to partially or completely increase, restore or replace the functional activity of a diseased or damaged soft tissue.

In a particular embodiment, the soft tissue is oral mucosa.

An additional aspect of the invention refers to a pharmaceutical composition comprising the biomaterial scaffold as defined above.

Another aspect of the invention relates to a cosmetic composition comprising the biomaterial scaffold as defined above.

The invention also relates to a method to partially or completely increase, restore or replace the functional activity of a diseases or damaged soft tissue, said method comprising the administration to a human or animal of a therapeutically effective amount of a biomaterial scaffold as defined above.

Another aspect of the invention relates to the use of a biomaterial scaffold as defined above in medicine.

The invention also relates to the use of a biomaterial scaffold as defined above to partially or completely increase, restore or replace the functional activity of a diseased or damaged soft tissue.

DETAILED DESCRIPTION OF THE INVENTION

Figure 1:
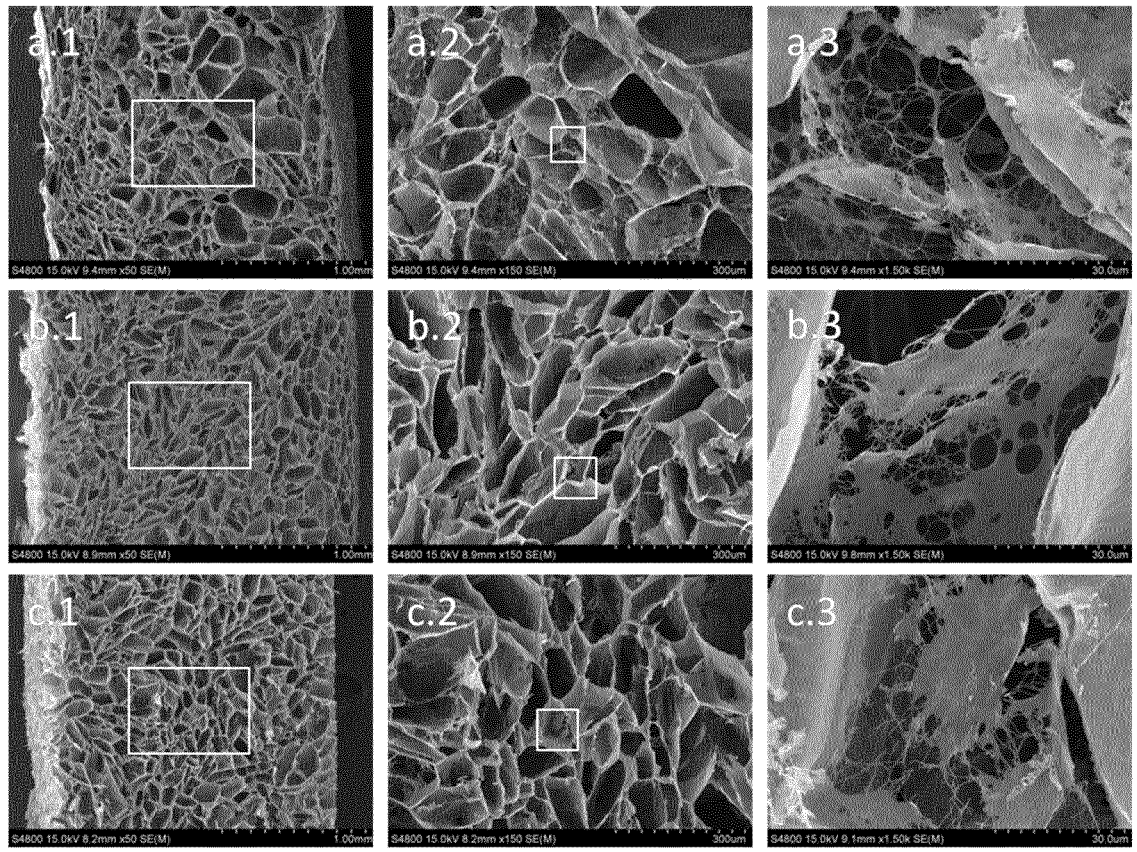
FIG. 1. Scanning Electron Microscopy micrographs of fibrin and agarose gels with different agarose concentration: a) 0.2%; b) 0.4%; c) 0.6%. Subindex 1, 2 and 3 correspond to different scales 50×, 150× and 1500× respectively.

The term "biomaterial" as used herein refers to a natural or synthetic biocompatible material that is suitable for being implanted into living tissue and which performs, augments, or replaces a natural function in a patient or subject. The biomaterial according to the present invention is particularly suitable for regenerating, replacing and/or repairing soft tissue defects or injuries by regenerating the tissue once it has been implanted into the site of the lesion.

By the term "scaffold" it is understood a highly porous tridimensional structure constituted by a network formed by association of macromolecules. This association between the macromolecules is provided chemically by strong or weak interactions (such as covalent bonds). This association results in a chemical cross-linking network. As a result of the performance of step b) of process 1, the association between the macromolecules is also provided physically, resulting in a physical and chemical cross-linking network.

Thus, in the present invention the biomaterial scaffold refers to a biomaterial as defined above with a scaffold structure.

As mentioned before, the process 1 of the invention for the production of a biomaterial scaffold comprises:
  a) providing a hydrogel comprising a fibrin network and a polysaccharide network;
  b) subjecting the hydrogel of step a) to a freeze-thawing process to physically crosslink the hydrogel; and
  c) subjecting the physically cross-linked hydrogel obtained after conducting the step b), to a lyophilization.

The first step of the process 1 of the present invention involves the provision of a hydrogel comprising a fibrin network and a polysaccharide network.

The term "hydrogel" is well known in the art, and it is understood as a gel having water as the liquid phase entrapped in what is commonly known as the solid phase. This solid phase constitutes a network which traps the liquid phase and prevents it from flowing.

The hydrogel provided in the first step of the process of the invention comprises a fibrin network. The terms "fibrin network", "fibrin matrix", "fibrin biomatrix", "fibrin-based scaffold", "fibrin scaffold", "fibrin gel", "fibrin adhesive" and "fibrin sealant" are often used interchangeably in the art to refer to a three-dimensional network resulting from the polymerization product of fibrinogen in the presence of a coagulation factor and a source of $Ca^{++}$. Such fibrin matrix is provided naturally by the body after injury, but also can be engineered as a tissue substitute.

Thus, in a particular embodiment, the fibrin network is obtained by polymerizing a fibrinogen-containing material in the presence of at least a coagulation factor and a calcium source.

In a preferred embodiment, the fibrinogen-containing material is of allogenic or xenogenic origin. Nevertheless, it may also be of autologous origin.

Fibrinogen is a high molecular weight protein present in blood plasma. Thus, the fibrinogen-containing material used as starting material for the generation of the fibrin network may be blood plasma or a plasma derivative, such as, for example, but not limited to a cryoprecipitate or fibrinogen concentrate. In this case, the coagulation factor is also present in the plasma, in particular, the coagulation factor is thrombin.

Thrombin is a proteolytic enzyme causing the rupture of fibrinogen molecule into low molecular weight polypeptides and fibrin monomers. Said monomers polymerize into dimers and are subsequently bound to one another by means of covalent bonds through the action of factor XIII, previously activated by the thrombin, and in the presence of calcium ions.

The concentration of fibrinogen used to prepare the fibrin network may vary and includes concentrations ranging from 1 mg/mL up to about 200 mg/mL (final concentration in the hydrogel). In a preferred embodiment, the fibrinogen is added at concentrations of about 1 to 5 mg/mL.

Further, the fibrinogen may be combined with any appropriate concentration of the coagulation factor. Preferably, the coagulation factor is thrombin.

Thrombin is added in varying concentrations ranging from about 0.1 IU/mL to about 300 IU/mL.

Preferably, the thrombin to fibrinogen ratio ranges from about 0.001 to about 100, more preferably from about 0.01 to about 10, even more preferably from about 0.1 to about 1.

In a particular embodiment, the hydrogel comprises fibrinogen at a final concentration from about 1 to about 100 mg/mL and thrombin at a final concentration from about 0.5 IU/mL to about 250 IU/mL.

In a particular embodiment, the polymerization of the fibrinogen-containing material is carried out also in the presence of other coagulation factors.

The term "coagulation factor" refers to a component, usually a protein present in blood plasma and involved in the chain reaction enabling coagulation. Suitable coagulation factors for use in the present invention include, without limitation, factor III (tissue factor or thromboplastin); factor IV; factor V (proaccelerin or labile factor); factor VI, factor VII (stable factor or proconvertin); factor VIII: (antihemophilic factor A or von Willebrand factor); factor IX (Antihemophilic B or Christmas factor), factor X (Stuart-Prower factor), factor XI (plasma thromboplastin antecedent): factor XII (Hageman factor), factor XIII (fibrin stabilizing factor), von Willebrand factor, high-molecular-weight kininogen (HMWK or Fitzgerald factor) and the like.

Thus, in the case of using blood plasma or a plasma derivative as fibrinogen-containing material, all molecules needed for polymerization of fibrinogen are contained therein and the fibrin network can be formed from plasma by the addition of a source of calcium.

In a preferred embodiment, the calcium source is a calcium salt, such as, without limitation, calcium chloride, calcium gluconate or a combination thereof. The concentration of calcium salt should be sufficient to induce polymerization of fibrinogen. In a more preferred embodiment, the salt calcium is calcium chloride. In a more preferred embodiment, the concentration of calcium chloride is between 0.1 and 3 g/L. However, lower or higher concentrations could also be used. In a particular embodiment, the fibrinogen-containing material is firstly diluted in water or in a saline solution, such as PBS.

The fibrin polymer can be degraded through a process called fibrinolysis. During fibrinolysis, plasminogen is converted into the active enzyme plasmin by tissue plasminogen activator (tPA). Plasmin binds to fibrin surface through its binding sites resulting in the degradation of fibrin. To prevent fibrinolysis of the hydrogel, the polymerization of the fibrinogen may be carried out in the presence of an antifibrinolytic agent such as, without limitation, epsilon aminocaproic acid, tranexamic acid or aprotinin. In a preferred embodiment, the antifibrinolytic agent is tranexamic acid.

Tranexamic acid is a synthetic derivative of the amino acid lysine with high affinity for lysine binding sites in plasminogen, being capable of blocking these sites and preventing binding of plasminogen activator to the surface of fibrin, exerting anantifibrinolitic effect. Tranexamic acid is advantageous over other antifibrinolytic agents of animal origin in that it does not transmit diseases. In a preferred embodiment, the concentration of tranexamic acid in the hydrogel is between 0.5 and 2 g/L, preferably 1 to 2 g/L. However, lower or higher concentrations could also be used.

Fibrin networks are very versatile, so they have been used for the development of different artificial tissues. However, the clinical use of these has been limited due to the fact mainly of low consistency, its difficult handling and its great fragility. For this reason, the hydrogel provided in step (a) of the process of the invention further comprises a polysaccharide network. In general, the polysaccharide is used to provide strength and consistency of the tissue, and should be soluble in it.

The term "polysaccharide network", as used herein, refers to a three-dimensional network resulting from the physical gelification of a polysaccharide. Polysaccharide networks usually form physical gels, i.e. gels which are not stabilized by chemical bonds between the components but rather by low-energy bonds (Van der Waals, hydrogen bonds, polar bonds, ionic bonds, etc.).

The polysaccharide may be any polysaccharide capable of forming a gel, preferably by a change of temperature, and may be selected from the group consisting of agarose, agar, cellulose, dextran, starch, chitosan, konjac, curdlan, carrageenan, pectin, gellan, and alginate. As the skilled person will understand, such gelled polysaccharide is advantageously comprised of one polysaccharide, but the present invention also embraces a mixture of two or more polysaccharides. In an advantageous embodiment of the present method, the polysaccharide is agarose.

Those skilled in the art will appreciate that suitable conditions for the gelling of the polysaccharide and formation of the polysaccharide network will depend on the nature of it. Thus, in the preferred case of the use of agarose as a polysaccharide, it is sufficient to reduce the temperature below the gelling temperature of agarose concentration. This temperature can be readily determined by one skilled in the art from tables that correlate the gelling temperature of agarose concentration in the sample (for example, the table available at http://www.lonzabio.com/uploads/tx_mwax-marketingmaterial/Lonza_BenchGuides_SourceBook_Appendix_B_-_Agarose_Physical_Chemistry.pdf In other embodiments, the invention contemplates the use of modified agaroses including, without limitation, methylagarose, hydroxyethylagarose, hydroxypropylagarose, allylagarose, acetylagarose and the like.

In a preferred embodiment the agarose is a low melting point agarose. Low melting point agarose is commercially available such as Ultra Pure (R) agarose (Invitrogen), NuSieve (R) GTG (R) Agarose (Lopza), LM Agarose and LM Sieve Agarose (Pronadisa) Agarose SERVA Premium (Serva) and the like. In the event that the polysaccharide network is formed by agarose, the formation of the polysaccharide network is carried out at a temperature of the mixture to 10-37° C., preferably 15-25° C., most preferably 20-25° C.

In a preferred embodiment, the polysaccharide network is formed by agarose. In another preferred embodiment, the concentration of agarose in the hydrogel is of about 0.05 to 1% and, preferably, from 0.2 to 0.6%.

The hydrogel provided in step (a) of the process of the invention is therefore obtained by performing a cross-linking reaction of fibrinogen into fibrin and by inducing the gelling of the polysaccharide. The skilled person will understand that both reactions can be carried out simultaneously or in any order, i.e. the polymerization of the fibrinogen into fibrin can be carried out first and be followed by the gelling of the polysaccharide or the gelling of the polysaccharide can be carried out first and be followed by the polymerization of the fibrinogen into the fibrin network.

In a particular embodiment, the fibrin network is firstly formed by placing a fibrinogen-containing material under conditions adequate for the formation of a fibrin network and then the polysaccharide matrix is formed by contacting the first network with a solution containing the polysaccharide and placing the mixture under conditions adequate for the formation of the polysaccharide network. In the particular case that the polysaccharide network is formed by agarose, formation of the agarose network can be achieved by placing the mixture at a temperature below the melting point of the agarose. Such temperature can be determined by the skilled person without further experimentation by consulting the melting profile of the particular agarose type being used.

However, in a preferred embodiment, the hydrogel comprising the fibrin network and the polysaccharide network is formed by first mixing a fibrinogen-containing material, a coagulation factor, a buffered saline solution, preferably PBS, and, optionally an antifibrinolytic agent. To this mixture, the polysaccharide and the source of calcium are added simultaneously, so that the fibrin network and the polysaccharide network are formed simultaneously upon subjecting the resulting mixture to conditions adequate for gelling of the polysaccharide, for example at a temperature below the melting point of the polysaccharide.

In a more preferred embodiment, the fibrinogen-containing material is blood plasma, the coagulation factor is thrombin which is included in blood plasma, the polysaccharide is agarose and the source of calcium is calcium chloride.

The second step (step b) of the process 1 of the invention comprises subjecting the hydrogel of step a) to a freeze-thawing process.

This freeze-thawing process induces the physical cross-linking of the hydrogel, and as a consequence of that, the hydrogel improves its mechanical properties, in particular, it provides the hydrogel with a higher strength, being also easily handled.

The freeze-thawing technique includes at least one cycle of freezing and thawing of the hydrogel, but preferably the physical cross-linking of the hydrogel is achieved by using a series of freeze-thaw cycles.

As a result of the freezing, optional storage in frozen state, and subsequent thawing of the hydrogel, a cryogel is formed. This cryogel is characterized for having a macroporous structure. During the freezing, the crystallization of the main bulk of the solvent (water) is formed. After thawing out, cryogels, or cryostructures are formed. Forced alignment of polymeric chains as the polymer concentration is increased by conversion of water to ice may provide a mechanism for the formation of side-by-side associations, which then remain intact on thawing, as the junction zones of the gel.

The three dimensional structure of the physically cross-linked gel is stabilized mainly by multiple interchain hydrogen bonds in the junction zones of the polymeric network.

By varying the regime in the cryogenic treatment, such as the temperature and the duration of freezing, rate of thawing, the number of refreezing cycles, it is possible to regulate and modulate the properties of the final gel and its macro- and micro-structures. Particularly, the stability and mechanical properties of the cryogel increases with increasing the freezing time and freeze-thaw cycles.

In a particular embodiment, the hydrogel obtained in step a) of the process of the invention is subjected to a freezing step by freezing it at a temperature comprised between −30° C. and −15° C., more preferably at about −20° C., during at least 6 hours, more preferably during at least 12 hours. Subsequently, the frozen hydrogel is thawed at room temperature, normally between 20 and 25° C., from 2 to 6 hours, more preferably during about 3 hours.

Although only one cycle of freeze-thaw is enough to provide the physical cross-linking to the hydrogel, it is recommended to perform several freeze-thaw cycles, preferably from 2 to 5 cycles.

In a particular embodiment, the process 1 of the invention further comprises washing the physically cross-linked hydrogel resulting from step b) of the process 1 of the invention.

The hydrogel resulting from step b) after carrying out the freeze-thawing process, can be simply washed with water in order to remove any compound or substance which does not form part of the three dimensional structure of the resulting material. For example, in the case of using plasma as fibrinogen-containing material, this washing step leads to the removal of those substances present in the plasma not being physically or chemically associated to the structure of the biomaterial.

After the washing step, the resulting hydrogel is white and odourless.

Step c) of the process 1 of the invention refers to the lyophilization of the physically cross-linked hydrogel resulting from step b), to obtain the biomaterial scaffold of the present invention.

From a pharmaceutical point of view, it is important to have the biomaterial available in lyophilised form since this improves its stability during storage.

Furthermore, the lyophilization allows providing the biomaterial with a controlled porosity, high strength, being easily handled in its swollen state and having stability, elasticity, flexibility and plasticity, as it can recover its shape after applying a deformation force. Furthermore, the biomaterial of the invention has shown to withstand a suture process in its swollen state without breaking or destroying, which assures correct fixing to the damaged tissue.

The hydrogel may be lyophilized by any method known by a skilled person, for example, in the presence of a cryoprotectant, such as glucose, sucrose or trehalose, at a 5% concentration. In fact, the biomaterial of the invention has the additional advantage that it can be lyophilised and resuspended without an alteration in the characteristics thereof.

However, the freezing method for lyophilization affects the pore size of biomaterial. The pore size in much larger in lyophilisates with gradual freezing, such as −1° C./min and smaller in lyophilisates that are rapidly frozen (for example, directly from room temperature to −80° C.).

For the same freezing method for lyophilization, it is seen that gels with high agarose concentration, such as 0.4 and 0.6%, have more similar structure, whereas lyophilisates with lower agarose concentration, such as 0.2%, have a significantly larger pore size.

For the same agarose concentration and different freezing method it is seen that a slow gradual freezing in the lyophilization provides a biomaterial with a uniform distribution of pores and better visual appearance. In fact, the ratio of the pores per unit area is different, corresponding to a ratio of 1:2 (slow freezing:rapid freezing). This translates into the fact that the lyophilisates that are rapidly frozen have twice the pores per unit area compared to lyophilisates that are gradually frozen. The pore is therefore smaller in lyophilisates that are rapidly frozen.

Thus, in a preferred embodiment, the lyophilization process is carried out by subjecting the hydrogel to a gradual freezing rate between 0.5° C./min to 5° C./min.

The resulting lyophilized biomaterial can also be subsequently subjected to a sterilization process without affecting its stability. Said process includes, for example, the application of gamma-radiation to the lyophilized product.

Sterilization processes are well-known by persons skilled in the art and are performed with the aim of being able to use the biomaterial in applications which require sterilized products as in the case of the present invention.

The process described herein provides a biomaterial that show advantageous properties with respect to other biomaterials used for regenerating soft tissues, in particular, with respect to compacted biomaterials obtained following processes such as those described in WO2011/023843 and WO2013/072409.

Particularly, the biomaterials exhibit a highly porous structure with a suitable interconnection or cross-linking to assure nutrient supply and cell waste elimination.

Furthermore, the resulting biomaterial can be easily swollen, being able to absorb liquid in proportions between 10 and 30 times its dry weight, depending on its initial composition. In its swollen state, it is highly resistant, has memory (recovers its shape after applying a deformation force to it) and it can be easily managed, also facilitating the surgical manipulation, thus facilitating the suture to the recipient bed and in vivo implantation. Thus, the swollen material can be compressed and folded without losing its properties, recovering its initial shape after deformation.

Additionally, the mechanical properties of the biomaterial are improved due to the physical cross-linking derived from the freeze-thawing step.

Another aspect of the invention refers to a process (process 2 of the invention) for preparing a physically cross-linked hydrogel having an interpenetrating network, said process comprising:
  a) providing a hydrogel comprising a fibrin network and a polysaccharide network; and
  b) subjecting the hydrogel of step a) to a freeze-thawing process.

Steps a) and b) of the process 2 can be carried out following the same procedures as those mentioned before in this specification for the case of the process 1 of the invention.

As mentioned before, the resulting hydrogel after conducting process 2 of the invention is a physically cross-linked hydrogel having an interpenetrating network. The physical cross-linking provides a hydrogel with improved mechanical properties.

Biomaterial of the Invention

The process 1 of the invention as defined above allows the production of a biomaterial with improved properties and which can be used for regenerating the oral mucosa. Therefore, in another aspect, the present invention refers to a biomaterial obtainable by the process 1 as defined above.

In another aspect, the invention relates to a porous biomaterial scaffold comprising a fibrin network and a polysaccharide network.

The biomaterial scaffold of the invention is highly porous with a suitable interconnection of the polymeric chains to assure nutrient supply and cell waste elimination.

In a particular embodiment, the biomaterial scaffold of the invention has a porous size ranging from 1 to 500 micron, preferably from 50 to 200 micron, more preferably from 50 to 100 micron.

Figure 2:
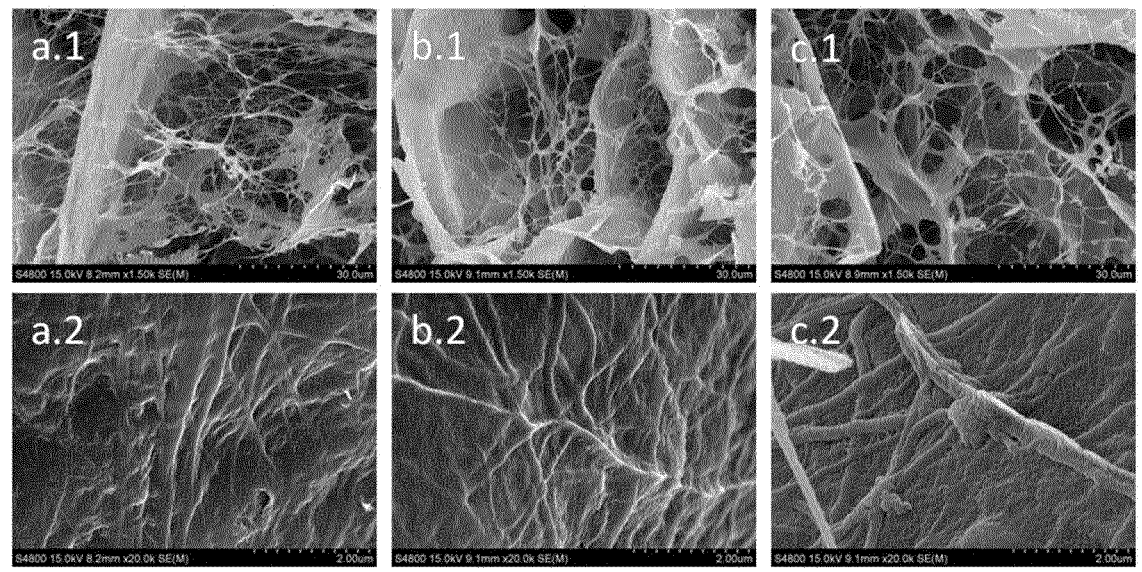
FIG. 2. Scanning Electron Microscopy micrographs showing in more detail the structure of the material with different compositions of agarose. Top row: 1.500×. Bottom row: 20.000×. a) 0.2% agarose; b) 0.4% agarose; c) 0.6% agarose.

The internal structure of the biomaterial scaffold of the invention has been analyzed by means of Scanning Electron Microscopy (SEM). FIGS. 1-2 correspond to the micrographs showing in detail the internal structure of the biomaterial scaffold at different scales using different polysaccharide concentrations.

Generally, an oval porous structure with a low interconnection between pores is observed. The pores do not seem to have a clear orientation throughout the material although they are indeed oriented by microareas.

As mentioned before, the biomaterial scaffold of the invention can be easily swollen, being able to absorb liquid in proportions between 10 and 30 times its dry weight depending on its initial composition. In its swollen state, it is highly resistant, has memory (recovers its shape after applying a deformation force to it) and it can be easily managed, also facilitating the surgical manipulation, thus facilitating the suture to the recipient bed and in vivo implantation. Thus, the swollen material can be compressed and folded without losing its properties, recovering its initial shape after deformation.

In a preferred embodiment, the porous biomaterial scaffold is obtained by first cross-linking a fibrinogen-containing material in the present of a polysaccharide under the conditions adequate for gelification of the polysaccharide. In yet another preferred embodiment, the cross-linking of the fibrinogen-containing material is performed in the presence of at least a coagulation factor, a calcium source and, optionally, an antifibrinolytic agent. In a preferred embodiment, after gelification, the resulting hydrogel is subjected to a freeze-thawing method such as that described above, before being subjected to the lyophilization step.

In another preferred embodiment, the porous biomaterial scaffold is obtained by simultaneous formation of the fibrin network and the polysaccharide network upon subjecting a mixture resulting from mixing a fibrinogen-containing material, a coagulation factor, a buffered saline solution, preferably PBS, and, optionally an antifibrinolytic agent, with a polysaccharide and a source of calcium, to conditions adequate for gelling of the polysaccharide, for example at a temperature below the melting point of the polysaccharide. After gelification, the resulting hydrogel is subjected to a freeze-thawing method such as that described above, before being subjected to the lyophilization step.

The biomaterial scaffold resulting from these preferred embodiments, in which the hydrogel is subjected to a freeze-thawing process, is also characterized in that it exhibits an improved strength due to the fact that the starting hydrogel is physically cross-linked as a consequence of having been subjected to a freeze-thawing process.

In both preferred embodiments, the fibrinogen-containing material is preferably blood plasma.

Also in both preferred embodiments, the coagulation factor is preferably thrombin. In yet another preferred embodiment, the calcium source is a calcium salt and, most preferably, calcium chloride. In yet another preferred embodiment, the antifibrinolytic agent is tranexamic acid.

In another preferred embodiment, the polysaccharide is agarose. In a still more preferred embodiment, the agarose is low-melting point agarose. In yet another preferred embodiment, the concentration of agarose in the biomaterial is of about 0.05 to 1% and more preferably, from 0.2 to 0.6%.

As shown in the examples provided in the present document, the porous biomaterial scaffold of the invention is characterized for being highly resistant, easily handled and for having memory as it recovers its shape after applying a deformation force. Furthermore, the biomaterial of the invention has shown to withstand, in its swollen state, a suture without breaking, which assures correct fixing to the damaged tissue.

The biological tests have also pointed out the correct interaction of the biomaterial with cells, in particular human fibroblasts, as well as a lack of cytotoxicity for said cells.

The porous biomaterial scaffold according to the invention may optionally contain one or more active ingredients such as one or more growth factors (e.g., in an amount ranging from 0.0000001 to 1 or 5 percent by weight of the matrix composition) to facilitate the regeneration of oral mucose. Examples of suitable active ingredients include, but are not limited to fibronectin, fibrin, laminin, acidic and basic fibroblast growth factors, testosterone, ganglioside GM-I, catalase, insulin-like growth factor-I (IGF-I), platelet-derived growth factor (PDGF), neuronal growth factor galectin-1, and combinations thereof. See, e.g., U.S. Pat. No. 6,506,727 to Hansson et al. and U.S. Pat. No. 6,890,531 to Horie et al. As used herein, "growth factors" include molecules that promote the regeneration, growth and survival of the mucosa tissue. Growth factors that are used in some embodiments of the present invention may be those naturally found in keratin extracts, or may be in the form of an additive, added to the keratin extracts or formed keratin matrices. Examples of growth factors include, but are not limited to platelet-derived growth factor (PDGF), erythropoietin (EPO), thrombopoietin (TPO), myostatin (GDF-8), growth differentiation factor-9 (GDF9), basic fibroblast growth factor (bFGF or FGF2), epidermal growth factor (EGF), hepatocyte growth factor (HGF), granulocyte-colony stimulating factor (G-CSF), and granulocyte-macrophage colony stimulating factor (GM-CSF). There are many structurally and evolutionarily related proteins that make up large families of growth factors.

Moreover, the porous biomaterial scaffold according to the invention may optionally comprise one or more immunomodulatory or bioactive compounds. As used herein an "immunosuppressive or immunomodulatory agent" is an agent that generally or specifically suppresses or modulates a mammalian immune response.

As used herein, the term "immunomodulator" includes cytokines, lymphokines, monokines, stem cell growth factors, lymphotoxins, hematopoietic factors, colony stimulating factors (CSF), interferons (IFN), parathyroid hormone, thyroxine, insulin, proinsulin, relaxin, prorelaxin, follicle stimulating hormone (FSH), thyroid stimulating hormone (TSH), luteinizing hormone (LH), hepatic growth factor, prostaglandin, fibroblast growth factor, prolactin, placental lactogen, OB protein, transforming growth factor (TGF), TGF-α, TGF-β, insulin-like growth factor (IGF), erythropoietin, thrombopoietin, tumor necrosis factor (TNF), TNF-α, TNF-beta, mullerian-inhibiting substance, mouse gonadotropin-associated peptide, inhibin, activin, vascular endothelial growth factor, integrin, interleukin (IL), granulocyte-colony stimulating factor (G-CSF), granulocyte macrophage-colony stimulating factor (GM-CSF), interferon-a, interferon-beta, interferon-γ, SI factor, IL-1, IL-2, IL-3, IL-4, IL-5, IL-6, IL-7, IL-8, IL-9, IL-10, IL-11, IL-12, IL-13, IL-14, IL-15, IL-16, IL-17, IL-18 IL-21, IL-25, LIF, kit-ligand, FLT-3, angiostatin, thrombospondin, endostatin, LT, and the like.

In another particular embodiment, the biomaterial scaffold further comprises an osteoconductive substance, such as calcium carbonates, bisphosphonates, hydroxyapatite or collagen. The incorporation of this substance is of particular relevance as guided bone regeneration when the biomaterial scaffold is used for hard tissue reconstruction.

In a particular embodiment of the invention, the biomaterial scaffold further comprises cells incorporated into the three-dimensional structure of the scaffold or in the surface thereof. The incorporation of cells enhances the regenerative activity of the biomaterial and the tissue repair process in those tissues highly damaged or without the possibility of in situ cellular contribution from the patient, since this biomaterial contains healthy cells of the same type as those present in the damaged tissue.

Preferably, the cells incorporated in the hydrogel are selected from the group consisting of fibroblasts, keratinocytes, myocytes, adipocytes, endothelial cells, undifferentiated mesenchymal stem cells or mesenchymal stem cells differentiated into another cell strain and/or undifferentiated hematopoietic stem cells or hematopoietic stem cells differentiated into another cell strain, ocular cells, corneal cells, retinal cells, epithelial cells, cells from leucocitary system, cells from hematopoietic system, chondrocytes, chondroblast, osteoblasts, osteocytes, neurons or other cells from the peripheric and central nervous system, cells from the white blood system and macrophages.

Therapeutic Use

Another aspect of the invention refers to a porous biomaterial scaffold as defined above for its use in medicine.

In another aspect, the invention refers to a porous biomaterial scaffold as defined above for its use to partially or completely increase, restore or replace the functional activity of soft tissues in humans and animals.

In a preferred embodiment, the invention refers to a porous biomaterial scaffold as defined above for its use to partially or completely increase, restore or replace the functional activity of a diseased or damaged soft tissues as a result of a dysfunction, an injury or a disease selected from the list comprising: a wound, an ulcer, a burn, a benign or malign neoplasm, an infection, a bruise, a traumatism, a caustication, a congenital malformation, a substance loss, oral mucosa or periodontal diseases.

In a more preferred embodiment, the invention refers to a porous biomaterial scaffold as defined above for its use to partially or completely increase, restore or replace the functional activity of the oral mucosa. More particularly, the porous biomaterial scaffold is used for the treatment of gingivitis, periodontitis and for repairing the periodontal ligament.

In another particular embodiment, the invention refers to a porous biomaterial scaffold as defined above for its use in the treatment or healing of wounds, burns, ulcers, scalds, fistulas or other chronic or necrotic wounds.

In another particular embodiment, the invention refers to a porous biomaterial scaffold as defined above for its use in the treatment of musculoskeletal injuries.

In another particular embodiment, the invention refers to a porous biomaterial scaffold as defined above for its use in the treatment of cardiovascular diseases.

In another particular embodiment, the invention refers to a porous biomaterial scaffold as defined above for its use in the treatment of ophthalmological diseases, such as corneal injuries or retinal injuries.

In another particular embodiment, the porous biomaterial scaffold as defined above is used for repairing the osteoarticular system, more particularly for repairing intervertebral disc diseases or cartilages, and for the treatment of osteoarthritis, periarthritis or arthrosis.

In another particular embodiment, the porous biomaterial scaffold as defined above is used for hard tissue regeneration, particularly for regeneration of periodontal tissues.

Another aspect of the invention relates to the use of a biomaterial scaffold as defined above in medicine.

The invention also relates to the use of a biomaterial scaffold as defined above to partially or completely increase, restore or replace the functional activity of a diseased or damaged soft tissue as defined above.

A further aspect of the invention relates to a pharmaceutical composition comprising the porous biomaterial scaffold of the invention.

In a preferred embodiment, the pharmaceutical composition comprises the porous biomaterial scaffold of the invention and also a pharmaceutically acceptable carrier. In another preferred embodiment, the pharmaceutical composition comprises the porous biomaterial scaffold of the invention and also an active ingredient. In a preferred embodiment, the pharmaceutical composition comprises the porous biomaterial scaffold of the invention and also an active ingredient together with a pharmaceutically acceptable carrier.

As used herein, the term "active ingredient" means any component which potentially provides a pharmacological activity or another different effect in diagnosing, curing, mitigating, treating, or preventing a disease, or which affects the structure or function of the human body or animal body.

The pharmaceutical compositions of the present invention can be used in a treatment method in an isolated manner or together with other pharmaceutical compounds or compositions.

Another aspect of the present invention refers to a cosmetic composition which comprises the porous biomaterial scaffold of the invention.

The cosmetic composition includes any composition which comprises the porous biomaterial scaffold of the invention and which is in the form of gel, cream, ointment or balm for its topical administration. Said compositions are characterized in that they have emollient, protective and regenerating properties even when they do not have any cosmetically active molecule associated.

In a variant of the invention, the cosmetic composition may also incorporate active molecules, although they do not have any therapeutic effect, they have properties as a cosmetic agent. Among the active molecules which may be incorporated in the antioxidant composition emollient agents, preservatives, fragrance substances, antiacne agents, antifungal agents, antioxidants, deodorants, antiperspirants, antidandruff agents, depigmenters, antiseborrheic agents, dyes, suntan lotions, UV light absorbers, enzymes, fragrance substances, among others, can be cited.

The cosmetic composition may further comprise pH controlling agents, such as, for example, buffer agents, which avoid the pH of the composition reducing to values below 5, as well as preservatives which avoid important structural changes in the composition. A person skilled in the art can determine which additional components can be used and if they are necessary, many of them being in common use in cosmetic compositions.

The invention will now be further described by way of reference to the following examples which are provided for the purpose of illustration only and should not be construed as being limiting on the invention.

EXAMPLES

Example 1. Preparation of the Biomaterial Scaffold

A solution containing a mixture of human blood plasma (76 ml), PBS 1× (16.5 ml) and Amchafibrin (1.5 ml) was prepared. Agarose 4% (5 ml) and calcium chloride 10% (1 ml) were added to said solution at the same time. The proportions are measured in v/v with respect to the total volume of the resulting mixture.

The resulting mixture was mixed thoroughly and added to a mold. The mixture was left to gel. FIG. 3(a) shows the resulting hydrogel prior to be subjected to lyophilization.

The hydrogel formed was washed gently with water and lyophilized. In that purpose hydrogels were frozen at −80° C. and water was sublimated afterwards at 0.024 mbar an −48° C.

Example 2. Preparation of the Biomaterial Scaffold and Physical Characterization Thereof A solution containing a mixture of human blood plasma (76 ml), PBS 1× (16.5 ml) and Amchafibrin (1.5 ml) was prepared. Agarose 4% (5 ml) and calcium chloride 10% (1 ml) were added to said solution at the same time. The proportions are measured in v/v with respect to the total volume of the resulting mixture.

The resulting mixture was mixed thoroughly and added to a mold. The mixture was left to gel.

The hydrogel formed was then subjected to a freezing-thawing process by freezing the hydrogel at −20° C. during 12 hours and subsequently the frozen hydrogel was thawed at room temperature during 3 hours.

Figure 3:
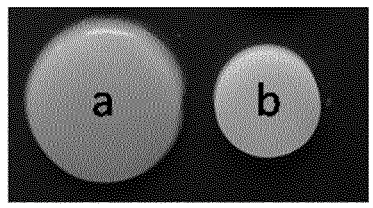
FIG. 3. Detail of the hydrogel of the invention obtained: (a) according to step a) of the process 1 of the invention; (b) according to steps a) and b) of the process 1 or 2 of the invention.

FIG. 3 (b) shows the resulting hydrogel prior to be subjected to lyophilization.

After that, the resulting hydrogel was washed gently with water and lyophilized. In that purpose hydrogels were frozen at −80° C. and water was sublimated afterwards at 0.024 mbar an −48° C.

The same procedure was followed but varying the agarose concentration to 0.2%, 0.4% and 0.6%.

FIG. 1 shows in detail the internal structure of the biomaterial scaffold for the different polysaccharide concentrations. Magnifications at 1,500× and 20,000× (FIG. 2) allow viewing in more detail fibrin networks filling up the pores of the structure as well as fibrin fibers most likely covered with agarose forming the wall of said pores.

Generally, an oval porous structure with a low interconnection between pores is observed. The pores do not seem to have a clear orientation throughout the material although they are indeed oriented by microareas.

Gels with higher agarose concentration, such as 0.4 and 0.6%, have more similar structure, whereas lower agarose concentration results in gels with a significantly larger pore size.

Figure 4:
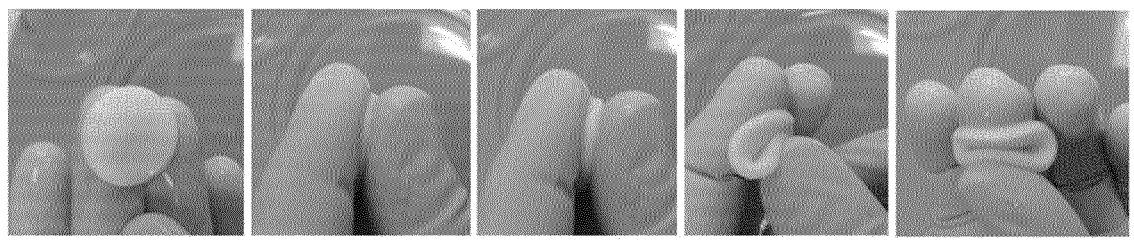
FIG. 4. Detail of the swollen biomaterial and its handling.

The material was also evaluated for manageability. Basic handling tests were conducted in the laboratory, evaluating performance visually. When it swells, the biomaterial is resistant, has memory (recovers its shape after applying a deformation force to it) and can be easily managed (see FIG. 4).

Figure 5:
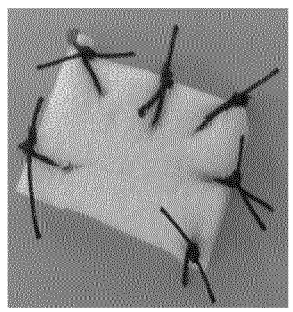
FIG. 5. Detail of the biomaterial after suturing its ends.

Additionally, suture tests were conducted in order to foresee the behavior of the biomaterial during a surgical intervention. It was observed that the biomaterial withstands said suture without breaking, assuring correct fixing to the tissue (see FIG. 5).

To evaluate the amount and volume of liquid that can be absorbed and stored by the biomaterial, samples having different agarose compositions were submerged in water.

The result shows that the biomaterial can absorb between 10 and 30 times its dry weight depending on its initial composition. The biomaterial swells fundamentally in the first 24 hour, this swelling increasing slightly thereafter.

Example 3. Biological Characterization of the Biomaterial

Live/Dead

Human fibroblasts cells were cultured for 24, 48 and 72 hours in a biomaterial prepared as described in example 2 with an agarose concentration of 0.2%.

A live/dead assay was conducted to evaluate cell viability. This assay allows distinguishing living cells from dead cells by means of a colorimetric method. Living cells emit green fluorescence due to their esterase activity. Deal cells however lack this activity and do not emit green fluorescence. To view the existence of dead cells the kit contains an ethidium homodimer, a compound that only penetrates cells with damaged membrane.

Figure 6:
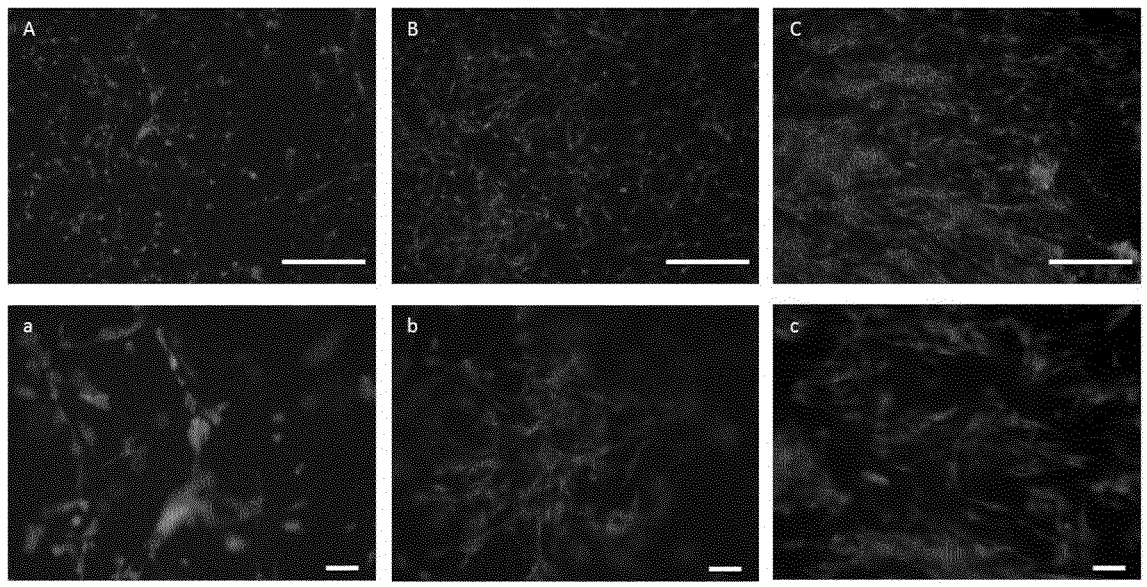
FIG. 6. Green/red fluorescence microphotographs of human fibroblasts cultured in the biomaterial of the invention (0.2% agarose). A, B and C: after culturing for 24, 48 and 72 hours, respectively. A, B and C correspond to a higher magnification of the microphotographs than a, b and c. The scale bar corresponds to 200 microns.
Figure 7:
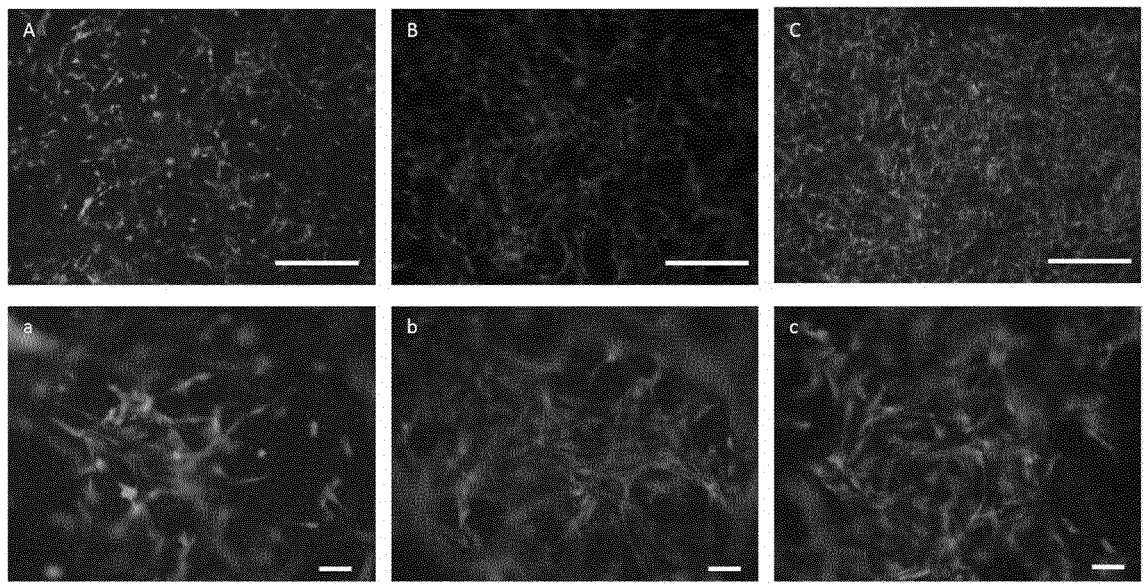
FIG. 7. Green/red fluorescence microphotographs of human fibroblasts cultured in the biomaterial of the invention (0.4% agarose). A, B and C: after culturing for 24, 48 and 72 hours, respectively. A, B and C correspond to a higher magnification of the microphotographs than a, b and c. The scale bar corresponds to 200 microns.

FIGS. 6 and 7 show the fluorescence results of the materials evaluated at different times. The cells extensively invade the three-dimensional structure and it increases in culture over time. No dead cells (red) are observed in any case.

This result translates into a positive interaction of the biomaterial with human fibroblasts.

Cytotoxicity

Cytotoxicity of the biomaterial prepared following example 2 was evaluated according to ISO 10993-5 standard (Biological Evaluation of Medical Devices. Part 5: Cytotoxicity Assay in vitro).

The assay was conducted with fibroblasts FA0506007 in pass 3 with a seeding density of 4000 cells/well in a 96-well plate.

Triplicates of two different compositions, having 0.2 and 0.4% agarose, were used in the assay.

Figure 8:
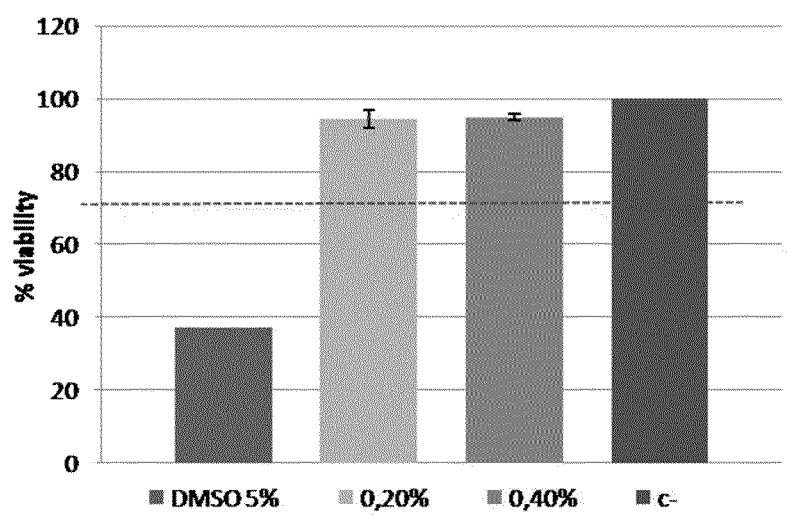
FIG. 8. Cell viability of human fibroblasts cultured on the biomaterial of the invention (0.2% and 0.4% agarose). The values represent the percentage of cell viability in relation to the control (100%). The dotted line marks the cytotoxicity limit according to ISO 10993:5.

The cytotoxicity result 24 hours post-culture shows that none of the materials is cytotoxic for the evaluated cells (see FIG. 8).

Hemocompatibility

Hemocompatibility was also evaluated according to ISO10993-4:2002 standard (Biological Evaluation of Medical Devices. Part 4: Selection of Tests for Interactions with Blood). The quantification of hemolytic effects is considered a specific determination due to the high plasma hemoglobin level in blood and determines the fragility of the erythrocyte membrane in contact with biomaterials.

Irritation Test

Figure 9:
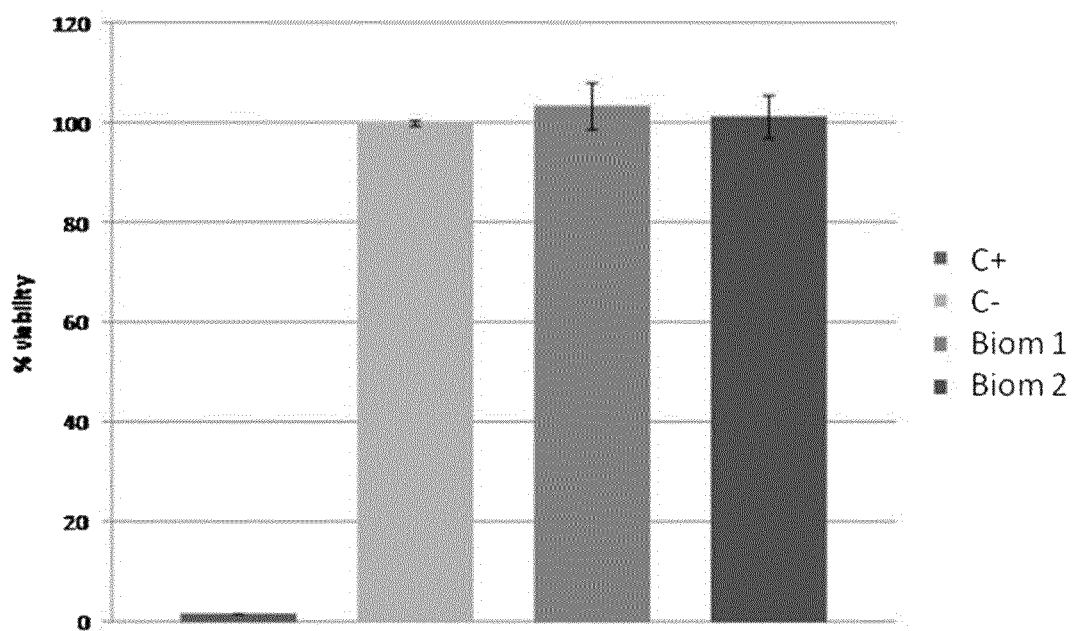
FIG. 9. Percentages of viability in positive control (irritant), negative control (reference viability) and samples (Biom 1 and Biom 2) according to the invention. The dotted line represents the limit used in this irritation model. Values above the line are considered NON-IRRITANTS whereas values below this line are considered IRRITANTS.

To analyze the possibility of the biomaterial being an irritant, two compositions according to example 2 (0.2% and 0.4% agarose) were analyzed. In both cases the material was analyzed in triplicate. The biomaterial is not an irritant for any of the analyzed compositions (see FIG. 9).

Example 3. In Vivo Proof-of-Principle

In a first approach, a biomaterial synthesized according to example 2 was subcutaneously implanted in a rat model in order to evaluate the response of the surrounding tissue to the biomaterial implanted in terms of potential toxicity events and degradability. Wistar AG rats more than 8 weeks of age were used in this study following housing and management according to Ethical Committee rules.

Figure 10:
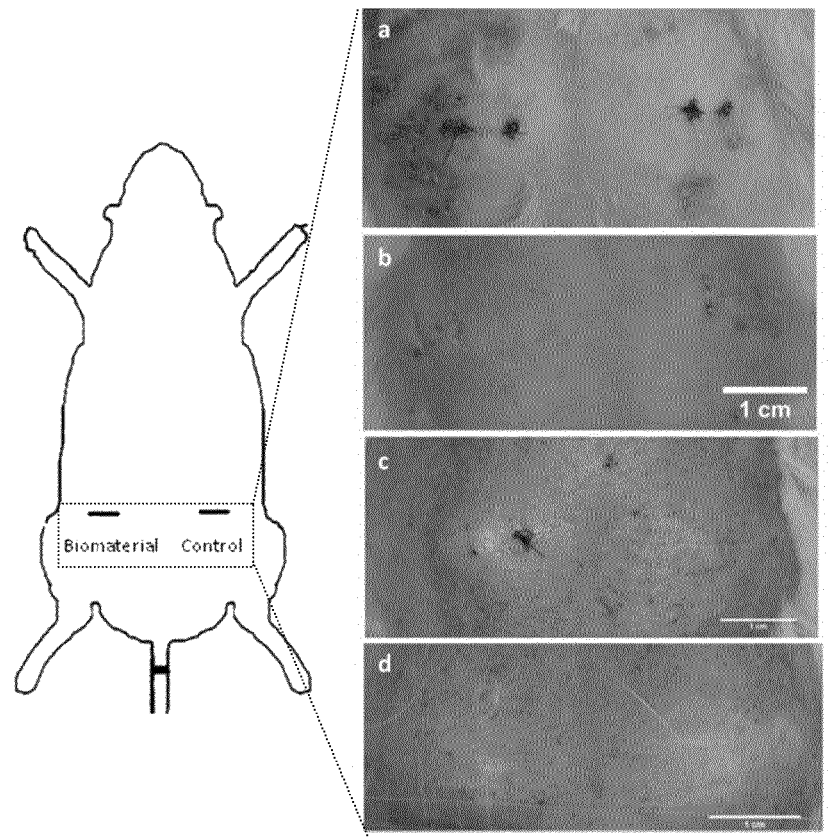
FIG. 10. Diagram of the implantation site of the materials in rats and images of biomaterial explants at different times: a) 7 days; b) 14 days; c) 30 days and d) 60 days.

In each animal, two incisions at both sides of the lower back were performed and 1 cm$^2$ of biomaterial was introduced subcutaneously through one of the incisions (see FIG. 10), leaving the other as control (physiological saline solution). At 7, 14, 30 and 60 days after biomaterial implanted, rats were sacrificed and biomaterial and surrounding tissues obtained for histological evaluation.

No signs of macroscopic external inflammation, erythema or edema were observed at any time of the experience in the adjacent tissues. Signs of neovascularization were observed both at day 7 and 14. A significant resorption of the biomaterial of the invention was observed after 30 days from implantation that continues progressively until the end of the assay at day 60.

TABLE 2

Size progression of the biomaterial of the invention throughout the testing time (60 days)

| | Area (cm$^2$) | | | |
|---|---|---|---|---|
| Days | 7 | 14 | 30 | 60 |
| Mean | 1.366 | 0.909 | 0.789 | 0.241 |
| Deviation | 0.107 | 0.207 | 0.034 | 0.035 |

The analysis of implant size progression shows a slight initial increase in the size of the biomaterial of the invention probably due to the biomaterial of the invention capacity for absorbing tissue fluids, recovering its initial size between days 7 and 14. From that time its size decreased progressively over time, demonstrating its resorption capacity along time without any surrounding tissue reaction. Anyway, apparent biomaterial collapse was not observed, whereby the matrix continues showing a three-dimensional structure.

Histological evaluation show that compared to control lesions, biomaterial at initial stages (7 days) is surrounded by a typical fibrotic capsule and immune cells recruitment that occur in all cases when an exogenous material is implanted. The results at 30 days already show a total resolution of this initial response while the formation of new vascular networks continues and a regular extracellular matrix can be observed in contact with the biomaterial of the invention.

Figure 11:
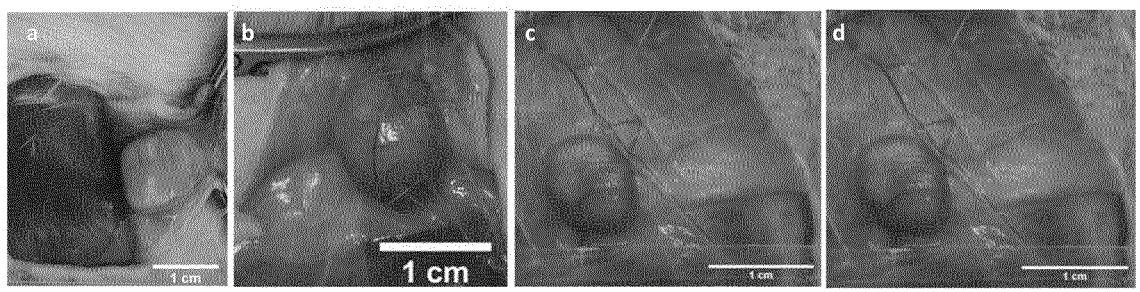
FIG. 11. Macroscopic image of the biomaterial explants throughout the testing time: a) 7 days; b) 14 days; c) 30 days and d) 60 days.
Figure 12:
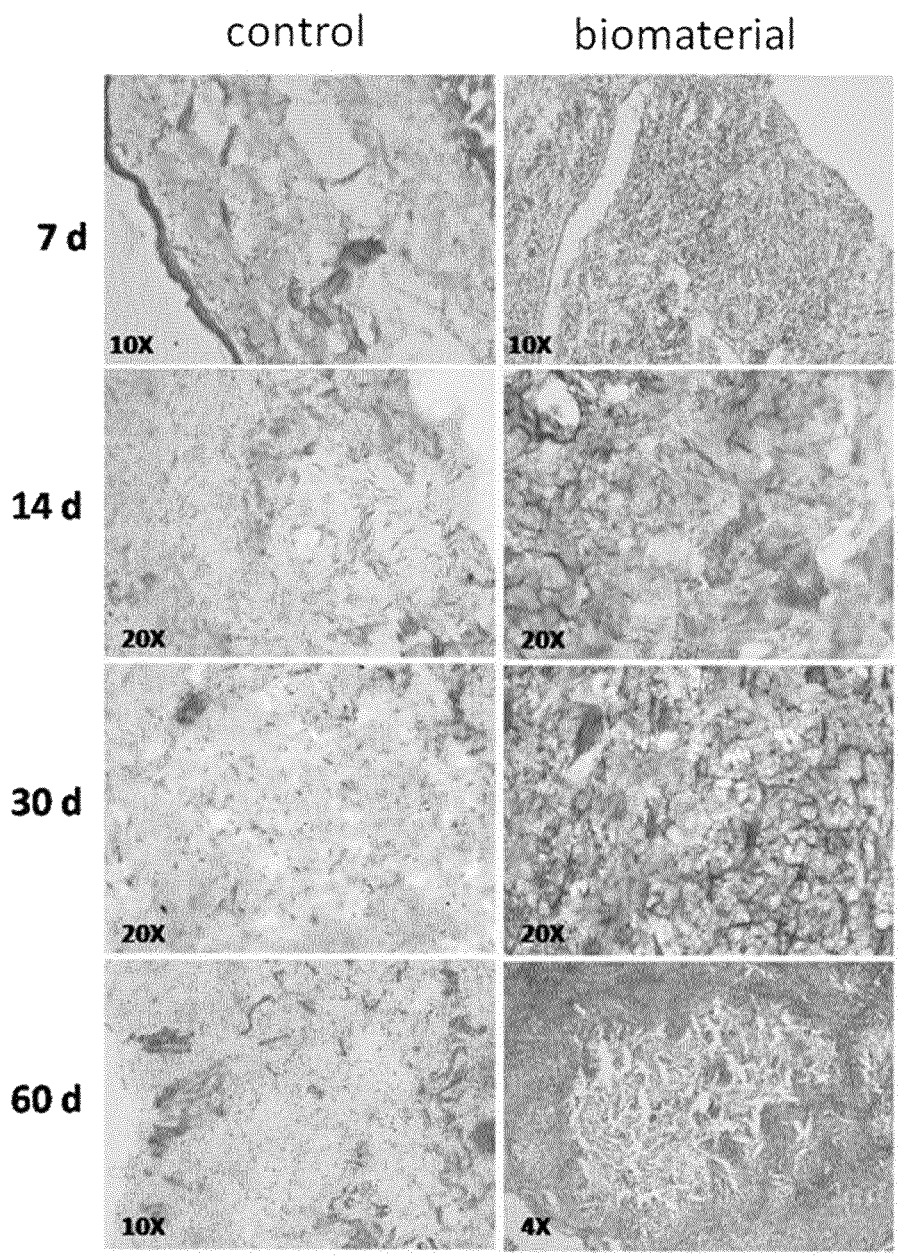
FIG. 12. Histological images of the explants throughout the testing time (7, 14, 30 and 60 days).
Figure 13:
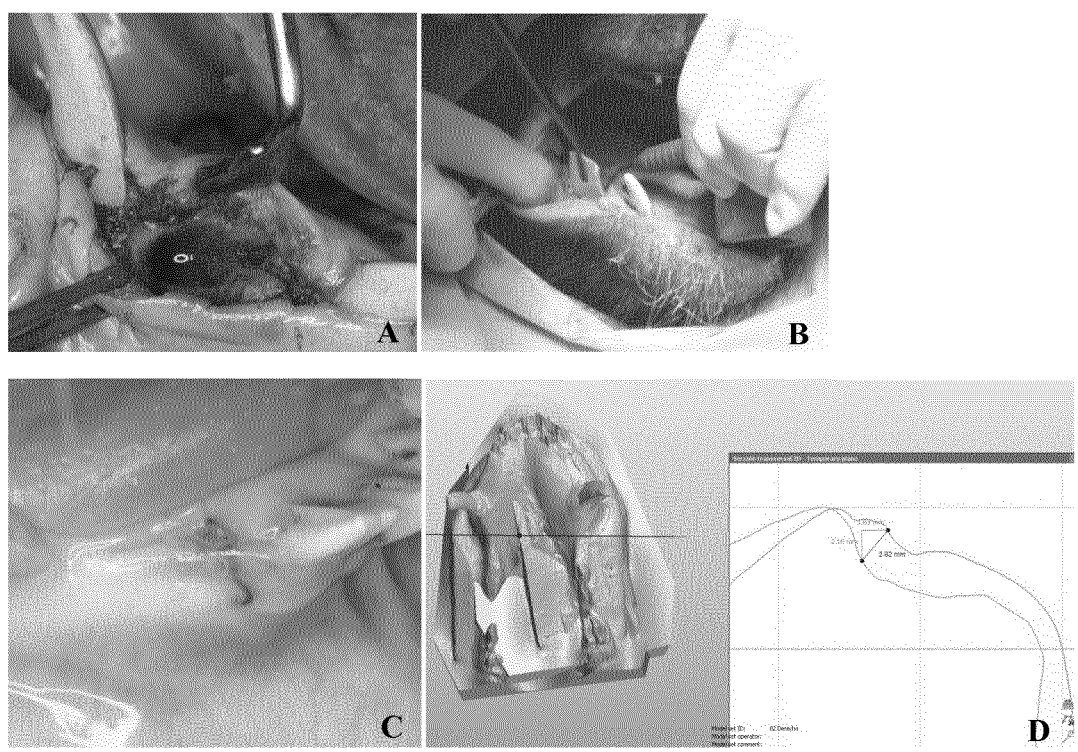
FIG. 13. In vivo proof of concept in oral mucosa defect in a minipig model: a) Oral mucosa defect after tooth extraction. b) Invention biomaterial implantation inside mucosa defect. c) Defect closure after biomaterial implantation with absorbable suture. d) Example of scanning of alginate cast models from animal jaw and image analysis through Ortho Viewer image analysis software.

FIG. 11 shows a macroscopic image of the biomaterial explants throughout the testing time (7, 14, 30 and 60 days), whereas FIG. 12 shows histological images of the explants throughout said testing time.

Example 4. In Vivo Proof-of-Concept

Biomaterial functionality was performed by assessment of the gingival volume increase after biomaterial implantation in an oral mucosa defect model in minipig.

Study was performed in a minipig in accordance with European regulations governing the care and treatment of laboratory animals and was approved by the Animal Care and Use Committee of the Universitat Autònoma de Barcelona. One male minipig of 35 kg body weight was selected and kept on a soft diet during all the study.

Extraction of incisors 3 and premolars 2 was performed in each side of the lower jaw. After a healing period of two months, alginate impressions and 3D scanning from each side of the lower jaw were obtained and a new surgery was performed for biomaterial implantation. Four lateral incisions and envelope flaps (1.5×2 cm) were originated at the lateral gingival mucosa of each tooth extraction and filled with biomaterial (1×1 cm). Additionally, in both sides, another incision was performed in the natural space between P1 and canine. Incision were completely closed with a absorbable monofilamental suture. At days 15, 45 and 90 after biomaterial implantation, 3D alginate impressions were performed and finally animal was sedated and euthanized. Biopsies (2×1 cm) for each gingival mucosa zone were obtained and seriated sections of 2 mm were routinely fixed in 10% neutral buffered formalin, paraffin embedded and hematoxylin and eosin stained. Macroscopic evaluation of tissue healing and control of food intake was performed along the experiment. Furthermore, master casts were made by mean of alginate impressions, cast models were scanned and processed with an image analysis software (Ortho-Viewer 2014 from 3Shape S/L) that allow different time models superimposition, longitudinal and transversal sections selection and detection of master differences. Means and standard deviation were calculated and volume differences analyzed.

No signs of biomaterial toxicity or any adverse events were observed during study in minipig. Biopsies showed a good dermal and epidermal tissue and no host reaction or inflammation due to biomaterial application was observed. It was produced a complete epithelial regeneration with presence of a multilayered, mature and queratinisated ephitelium. Submucosa showed a well organized connective tissue, with mature collagen composed of thick, dense and well organized fibers. Biomaterial was almost completely disappeared.

Cast models volume analysis showed a volume gain in lesions when biomaterial has been implanted, as indicated in table 3.

TABLE 3

Increase in gingival mucosa volume caused by biomaterial implantation oral mucosa defects.

| Zone | Final Volume Increase (mm) |
| --- | --- |
| Incision 1 | 1.07 |
| Incision 2 | 0.88 |
| Incision 3 | 1.98 |
| Incision 4 | 1.37 |
| Mean ± SD | 1.33 ± 0.5 |

Biomaterial implantation produced an important gingival volume increment that is very similar to volume gain obtained when autologous subephitelial connective tissue graft (graft from a donor site of patient own tissue) is applied.

The invention claimed is:

1. A method for producing a biomaterial scaffold, said method comprising:
   a) providing a hydrogel comprising a fibrin network and a polysaccharide network, wherein the polysaccharide network comprises agarose;
   b) subjecting the hydrogel of step a) to a freeze-thawing process to physically crosslink the hydrogel; and
   c) subjecting the physically cross-linked hydrogel obtained after conducting step b) to a lyophilization process at a gradual freezing rate; wherein the hydrogel has a concentration of agarose of about 0.2% to 1%.

2. The method according to claim 1, wherein the fibrin network is obtained by polymerizing a fibrinogen-containing material.

3. The method according to claim 2, wherein the fibrinogen-containing material is blood plasma.

4. The method according to claim 2, wherein the polymerization of the fibrinogen-containing material is carried out in the presence of a coagulation agent, a calcium source and, optionally, in the presence of an antifibrinolytic agent.

5. The method according to claim 4, wherein the calcium source is a calcium salt.

6. The method according to claim 1, wherein the polysaccharide network is obtained by gelling agarose.

7. A biomaterial scaffold obtainable by the process as defined in claim 1.

8. A biomaterial scaffold according to claim 7, wherein said biomaterial scaffold comprises cells incorporated into the structure of the scaffold or on the surface thereof.

9. A pharmaceutical composition comprising the biomaterial scaffold as defined in claim 7.

10. A cosmetic composition comprising the biomaterial scaffold as defined in claim 7.

11. The method according to claim 3, wherein the polymerization of the fibrinogen-containing material is carried out in the presence of a coagulation agent, a calcium source and, optionally, in the presence of an antifibrinolytic agent.

12. A pharmaceutical composition comprising the biomaterial scaffold as defined in claim 8.

13. A cosmetic composition comprising the biomaterial scaffold as defined in claim 8.

14. The method according to claim 1, wherein the lyophilization process is carried out by subjecting the hydrogel to a gradual freezing rate between 0.5° C./min to 5° C./min.

15. The method according to claim 1, wherein the hydrogel has a concentration of agarose of about 0.2% to 0.6%.

* * * * *